United States Patent
Nakajima et al.

(10) Patent No.: US 9,271,882 B2
(45) Date of Patent: Mar. 1, 2016

(54) ABSORBENT ARTICLE

(75) Inventors: Kaiyo Nakajima, Kagawa (JP); Haruki Toda, Kagawa (JP)

(73) Assignee: Unicharm Corporation, Ehime (JP)

(*) Notice: Subject to any disclaimer, the term of this patent is extended or adjusted under 35 U.S.C. 154(b) by 189 days.

(21) Appl. No.: 13/824,497

(22) PCT Filed: Nov. 14, 2011

(86) PCT No.: PCT/JP2011/076615
§ 371 (c)(1),
(2), (4) Date: Mar. 18, 2013

(87) PCT Pub. No.: WO2012/067218
PCT Pub. Date: May 24, 2012

(65) Prior Publication Data
US 2013/0237941 A1    Sep. 12, 2013

(30) Foreign Application Priority Data
Nov. 19, 2010 (JP) ................................. 2010-259457

(51) Int. Cl.
*A61F 13/15* (2006.01)
*A61F 13/537* (2006.01)
(Continued)

(52) U.S. Cl.
CPC ............. *A61F 13/537* (2013.01); *A61F 13/535* (2013.01); *A61F 13/495* (2013.01); *A61F 2013/4953* (2013.01); *A61F 2013/4956* (2013.01); *A61F 2013/4958* (2013.01)

(58) Field of Classification Search
CPC ........... A61F 13/495; A61F 2013/4953; A61F 2013/4956; A61F 2013/4958
USPC ............... 604/378, 379, 380, 383, 385.01, 604/385.101, 395
See application file for complete search history.

(56) References Cited

U.S. PATENT DOCUMENTS

| | | | |
|---|---|---|---|
| 2002/0013568 A1* | 1/2002 | Cinelli et al. | ................. 604/387 |
| 2006/0184146 A1 | 8/2006 | Suzuki | |
| 2007/0093164 A1 | 4/2007 | Nakaoka | |

FOREIGN PATENT DOCUMENTS

| | | |
|---|---|---|
| EP | 0 689 815 A1 | 1/1996 |
| JP | 2003-93441 A | 4/2003 |

(Continued)

OTHER PUBLICATIONS

International Search Report from corresponding PCT application No. PCT/JP2011/076615 dated Feb. 14, 2012 (2 pgs).
(Continued)

*Primary Examiner* — Jacqueline Stephens
(74) *Attorney, Agent, or Firm* — Brinks Gilson & Lione (57) ABSTRACT

An absorbent article configured to ensure that even when the excreted urine diffuses by running down the wearer's skin, the skin is prevented from remaining wetted. In the absorbent article of the present invention, when an artificial urine is dropped and absorbed in the urination region of the crotch region, where an absorbent sheet is not disposed, the return amount of the artificial urine in the buttock region of the rear waist region, where an absorbent sheet is disposed, takes a value of 200 times less than the return amount of the artificial urine in the urination region; and the return amount of the artificial urine in the buttock region when the artificial urine is dropped and absorbed in the buttock region takes a value of 0.7 or less of the return amount of the artificial urine in the urination region when the artificial urine is dropped and absorbed in the urination region.

20 Claims, 7 Drawing Sheets

(51) Int. Cl.
*A61F 13/535* (2006.01)
*A61F 13/495* (2006.01)

(56) References Cited

FOREIGN PATENT DOCUMENTS

| JP | 2004-275225 A | 10/2004 |
| JP | 2004/329664 A | 11/2004 |
| JP | 2005-6954 A | 1/2005 |
| JP | 2008-284190 A | 11/2008 |
| JP | 2009-28186 A | 2/2009 |

OTHER PUBLICATIONS

European extended Search Report from corresponding European application No. 11842000.9 dated Mar. 5, 2014 (5 pgs).

* cited by examiner

ABSORBENT ARTICLE

RELATED APPLICATION

This application is a 35 U.S.C. §371 national phase filing of International Patent Application No. PCT/JP2011/076615, filed Nov. 14, 2011, through which and to which priority is claimed under 35 U.S.C. §119 to Japanese Patent Application No. 2010-259457, filed Nov. 19, 2010.

TECHNICAL FIELD

The present invention relates to an absorbent article. More specifically, the present invention relates to an absorbent article such as urine-absorbing pad, disposable diaper, toilet training pant and incontinence brief.

BACKGROUND ART

An absorbent article comprising an absorption body, a topsheet disposed to cover the front surface of the absorption body and at least partially composed of a liquid-pervious material, and a backsheet disposed on the back surface of the absorption body and composed of a liquid-impervious material, wherein the absorption body has a hole part formed to extend from the front surface to the back surface of the absorption body at least in a region corresponding to the wearer's excretory site (excretory region), a diffusion sheet is disposed on the back surface of the absorption body to cover the opening of the hole part at least in the excretory region while arranging the topsheet on the front surface of the absorption body, and a water-repellent sheet is disposed in a region above the diffusion sheet, which is located behind the excretory region when wearing, is known as a conventional technique (see, for example, Patent Literature 1).

This absorbent article is not only excellent in the absorptivity of a liquid excrement but also can effectively prevent a return of the liquid excrement. That is, in the absorbent article above, a liquid excrement is absorbed at the excretory site in the topsheet side surface (front surface) of the absorption body and at the same time, the liquid excrement is partially allowed to pass through the hole part and permeate the diffusion sheet, whereby the liquid excrement can be absorbed from the back surface of the absorption body by way of the diffusion sheet. In this way, since a liquid excrement can be absorbed in a wider region, the liquid excrement can be absorbed at a high absorption rate with excellent absorptivity. Also, the absorption body comprises a water-repellent sheet disposed in a region above the diffusion sheet, which is located behind the excretory region on wearing, so that in the buttock region where a body pressure is readily imposed during wearing and a liquid excrement is liable to cause a return, seepage of the liquid excrement to the absorption body surface can be limited and a return of the liquid excrement can be effectively prevented.

CITATION LIST

Patent Literature

[Patent Literature 1] Kokai (Japanese Unexamined Patent Publication) No. 2009-28186

SUMMARY OF THE INVENTION

Technical Problem

However, the conventional absorbent article described in Patent Document 1 sometimes faces a problem that when the wearer's urination orifice is not contacted with the absorbent article, the excreted urine diffuses by running down a wearer's skin, as a result, the urine is spread on the water-repellent sheet in the rear part and the skin remains wetted with urine.

Solution to Problem

In order to solve the problem above, the present invention employs the following configuration.

That is, the present invention is an absorbent article consisting of a front waist region, a rear waist region and a crotch region located between these regions in a longitudinal direction from a front side to a rear side, comprising a liquid-pervious topsheet, a backsheet, an absorption body intervening between the topsheet and the backsheet, and, an absorbent sheet between said topsheet and said absorption body, comprising at least one liquid-pervious sheet having sandwiched thereby an absorbent polymer, wherein: the topsheet, the backsheet and the absorption body are disposed across the front waist region, the crotch region and the rear waist region; the absorbent sheet is disposed in at least a part of the rear waist; the absorbent article has a urination region that is a region having not disposed therein the absorbent sheet and covering the wearer's urination orifice, and a buttock region that is a region having disposed therein the absorbent sheet and covering the wearer's buttocks; when artificial urine is dropped and absorbed in the urination region; the artificial urine comprises 200 g of urea, 80 g of sodium chloride, 80 g of magnesium sulfate, 8 g of calcium chloride and about 1 g of a dye per 10 liters of ion-exchanged water; and the return amount of the artificial urine in the buttock region has a value of 200 times less than the return amount of the artificial urine in the urination region; and the return amount of the artificial urine in the buttock region when the artificial urine is dropped and absorbed in the buttock region has a value of 0.7 or less of the return amount of the artificial urine in the urination region when the artificial urine is absorbed in the urination region. Also, in the absorbent article of the present invention, when an artificial urine is dropped and absorbed from the urination region, the surface residual water quantity in the buttock region has value of 0.8 or less of the surface residual water quantity in the urination region.

Advantageous Effects of the Invention

According to the present invention, even when the excreted urine diffuses by running down a wearer's skin, the skin of buttocks is prevented from remaining wetted with urine, i.e., the wearer's skin can be kept in a dry, comfortable state.

DESCRIPTION OF EMBODIMENTS

The absorbent article according to one embodiment of the present invention is described below by referring to the drawings. The absorbent article according to one embodiment of the present invention is a urine-absorbing pad.

Figure 1:
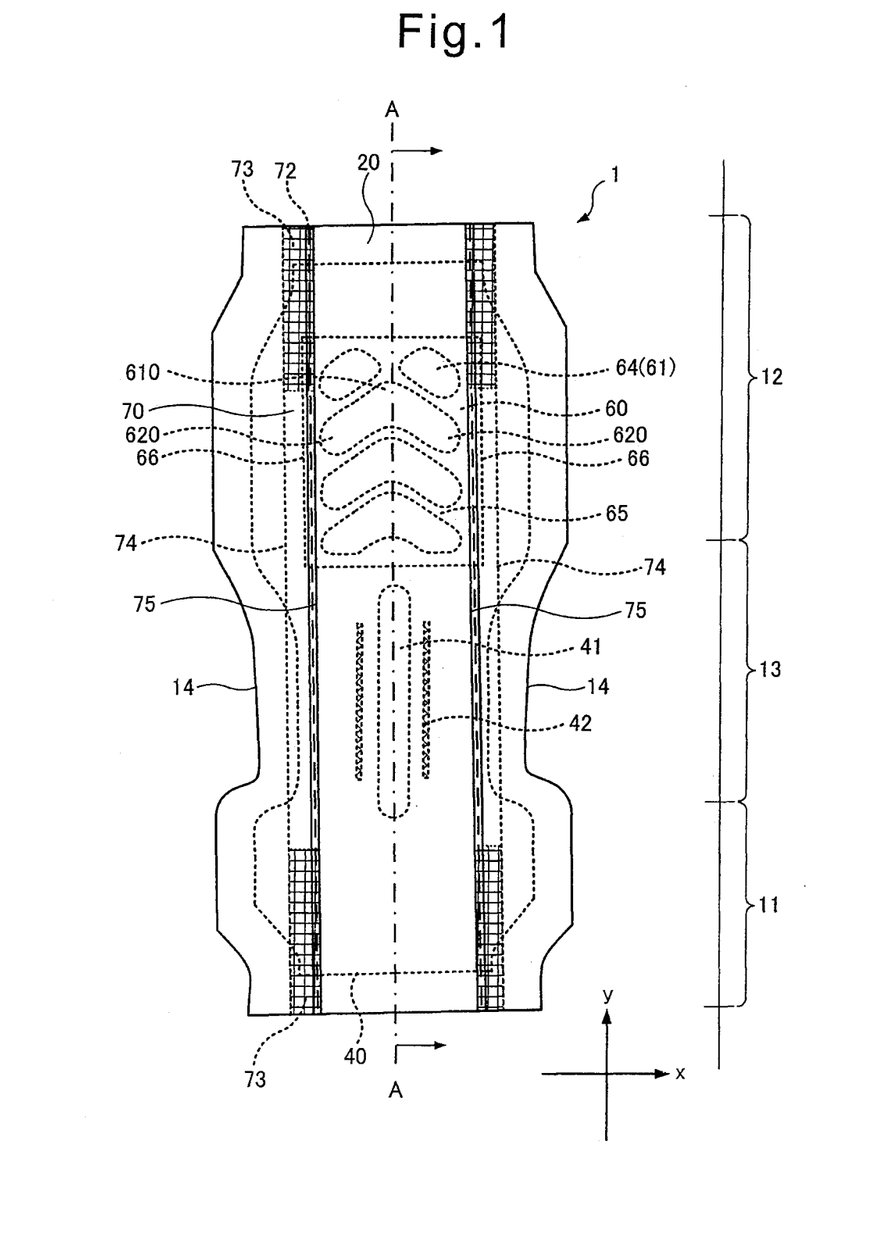
FIG. 1 is a plan view of the absorbent article according to one embodiment of the present invention when viewed from the wearer's skin side.
Figure 2:
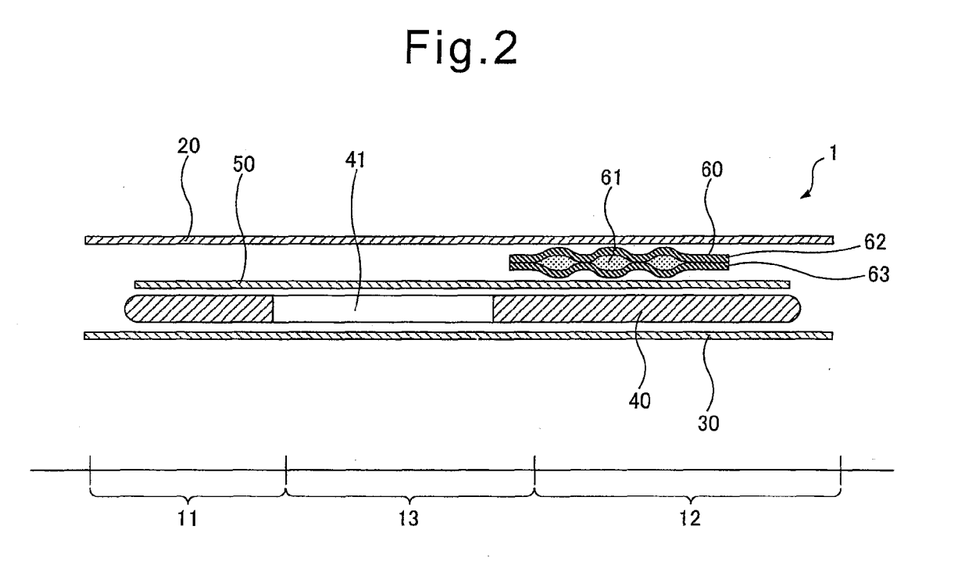
FIG. 2 is a schematic view of the A-A cross-section of FIG. 1.
Figure 3:
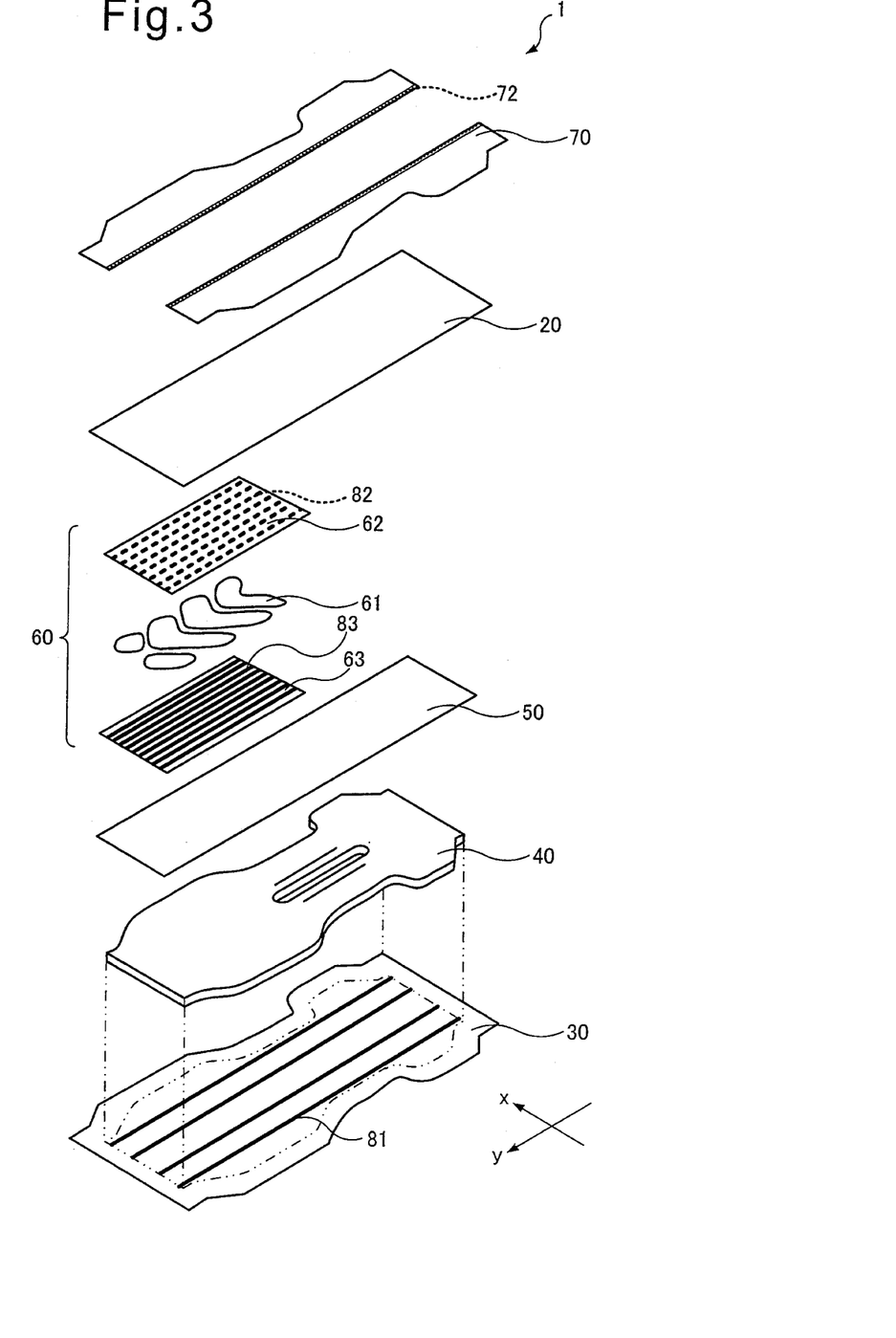
FIG. 3 is an exploded view of the absorbent article according to one embodiment of the present invention.
Figure 4:
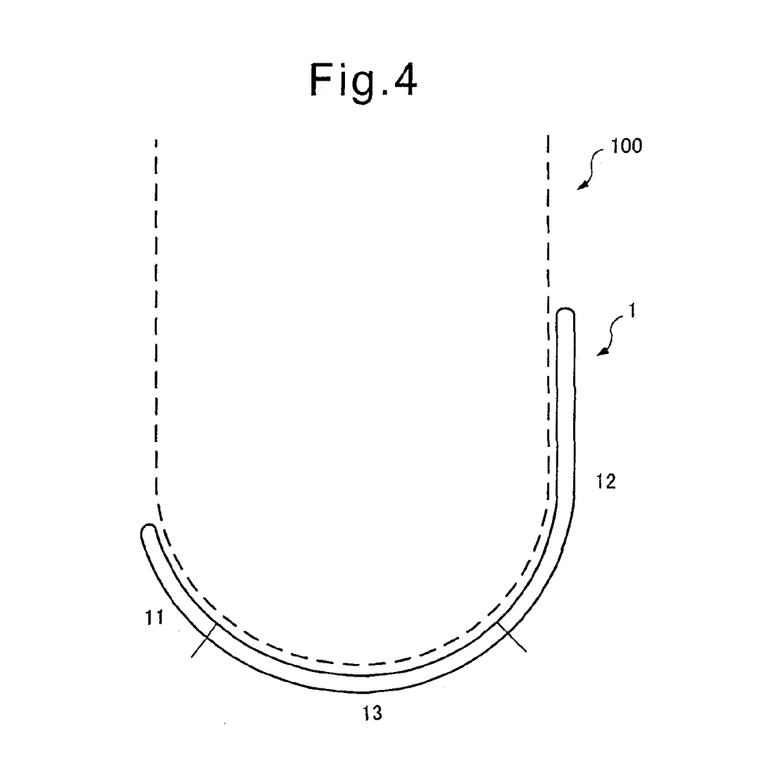
FIG. 4 is a view showing the worn state of the absorbent article according to one embodiment of the present invention.

FIG. 1 is a plan view of the absorbent article according to one embodiment of the present invention when viewed from the wearer's skin side, FIG. 2 is a schematic view of the A-A cross-section of FIG. 1, FIG. 3 is an exploded view of the absorbent article according to one embodiment of the present invention, and FIG. 4 is a view showing the worn state of the absorbent article according to one embodiment of the present invention. The x-axis direction shown in the Figures is the width direction of the absorbent article 1, the y-axis direction is the longitudinal direction of the absorbent article 1, and the xy direction is the planar direction of the absorbent article 1.

As shown in FIG. 1, the absorbent article 1 is divided into a front waist region 11, a rear waist region 12, and a crotch region 13 between the front waist region 11 and the rear waist region 12. Here, the front waist region 11 side of the absorbent article 1 is taken as the front side and the rear waist region 12 side of the absorbent article 1 is taken as the rear side. As shown in FIG. 4, the crotch region 13 is a region applied to the crotch part of a wearer 100 when the absorbent article is worn, the front waist region 11 is a region on the front side relative to the crotch region 13, and the rear waist region 12 is a region on the rear side relative to the crotch region 13. In the crotch region 13, the side part 14 (see FIG. 1) is bent or curved to decrease the dimension in the width direction of the absorbent article 1. The "crotch part" as used herein indicates the region between both femoral areas of the wearer when the wearer stands erect. Accordingly, the front waist region 11 covers the belly side of the wearer, and the rear waist region 12 covers the dorsal side of the wearer. That is, the crotch region 13 is a region applied to the wearer's crotch part, the front waist region 11 is a region covering the front side relative to the wearer's crotch part, and the rear waist region 12 is a region covering the rear side relative to the wearer's crotch part. Also, the region covering the wearer's urination orifice is referred to as the urination region, and the region covering the wearer's buttocks is referred to as the buttock region.

The absorbent article 1 in one embodiment of the present invention comprises a liquid-pervious topsheet 20, a backsheet 30 provided at the position opposing the topsheet 20, and an absorption body 40 provided between the topsheet 20 and the backsheet 30. A second sheet 50 is disposed between the topsheet 20 and the absorption body 40, and an absorbent sheet 60 is disposed between the topsheet 20 and the second sheet 50. On both widthwise sides of the absorbent article 1, a leak-preventive cuff 70 is disposed. Hereinafter, the urination region where the absorbent sheet 60 is not disposed is simply referred to as an urination region, and the buttock region where the absorbent sheet 60 is disposed is simply referred to as the buttock region.

The topsheet 20 is a liquid-pervious sheet allowing the excreted urine to permeate therethrough and is provided on the surface coming into contact with the wearer's skin when the wearer wears the absorbent article 1. Accordingly, the topsheet 20 preferably has a function of giving a soft and comfortable touch to skin. For example, the topsheet 20 can be produced using a fine fiber and have smooth surface and large latitude for deformation. Generally, a nonwoven fabric is used for the topsheet 20. Examples of the nonwoven fabric used for the topsheet 20 include a spunbond nonwoven fabric, a point bond nonwoven fabric and an air-through nonwoven fabric. The topsheet 20 is disposed across the front waist region 11, the crotch region 13 and the rear waist region 12.

The backsheet 30 is a liquid-impervious sheet allowing no permeation of urine and is provided to prevent the excreted urine from leaking outside. The material of the backsheet 30 is not particularly limited as long as it is a material allowing no permeation of excreted urine. For example, a waterproof-treated nonwoven fabric, a plastic film composed of polyethylene or the like, or a composite material of nonwoven fabric and plastic film can be used for the backsheet 30. Also, in order to prevent the absorbent article 1 from causing stuffiness when worn due to exhalation of water vapor through the backsheet 30, a breathable film may be used for the backsheet 30. Incidentally, in the case of a urine-absorbing pad or the like used inside a diaper, the backsheet need not be liquid-impervious. The backsheet 30 is disposed across the front waist region 11, the crotch region 13 and the rear waist region 12.

The absorption body 40 has a function of absorbing and holding the excreted urine. The absorption body 40 includes, for example, an absorption body composed of a fluffed pulp or an air-laid nonwoven fabric and a super-absorbent polymer (SAP). The absorption body 40 may alternatively include, for example, a fiber network absorption body using a chemical pulp, a cellulose fiber, an artificial cellulose fiber such as rayon and acetate, or a synthetic fiber (including a composite fiber) such as polyolefin, polyester and polyamide, or a foam absorption body using a foam material such as polyurethane, instead of using a fluffed pulp.

The absorption body 40 has a nearly similar shape as the backsheet 30 and the size of the absorption body 40 is smaller than the backsheet 30. The absorption body 40 is disposed across the front waist region 11, the crotch region 13 and the rear waist region 12. The absorption body 40 has a penetration part 41 and compressed grooves 42. The penetration part 41 is a hole penetrating the absorption body 40 in the thickness direction and at the widthwise central position of the absorption body 40, the penetration part 41 longitudinally extends across the crotch region 13 up to or into the front waist region 11. However, the penetration part 41 of the absorption body 40 is kept from longitudinally extending into the region of the absorption body 40, where the absorbent sheet 60 is disposed. The compressed grooves 42 are disposed on both sides of the penetration part 41 in alignment with each other and are grooves longitudinally extending across the crotch region 13 and are dented from the topsheet side surface of the absorption body 40. The longitudinal length of the compressed grooves 42 is shorter than the longitudinal length of the penetration part 41. The compressed grooves 42 are formed by heating pressurizing the absorption body 40 toward the backsheet 30 side surface from the topsheet 20 side surface of the absorption body 40. The absorption body 40 is adhered to the backsheet 30 by a hot-melt adhesive (HMA) 81. The absorption body 40 may be in a rectangular, oval or the like form instead of having a nearly similar as the backsheet 30.

Incidentally, in place of the penetration part 41, a groove part where the absorption body 40 is dented from the topsheet 20 side surface of the absorption body 40 and thereby reduced in the thickness may be provided. Furthermore, two or more absorption bodies may be disposed in the absorbent article. For example, in place of the absorption body 40, a stack prepared by stacking two absorption bodies in the thickness direction may be disposed in the absorbent article. Also, in this case, out of two absorption bodies, the penetration part or groove part may be provided only in the absorption body on the second sheet side or only in the absorption body on the topsheet 20 side. In addition, the penetration part or groove part of the absorption body may be designed to longitudinally extend even into the region of the absorption body, where the absorbent sheet 60 is disposed. Thanks to this configuration, the excreted urine can rapidly move to the lower side of the absorbent sheet 60 and therefore, a larger amount of urine absorbed by the absorption body 40 is less likely to reach the wearer's skin side due to the absorbent sheet 60.

The second sheet 50 is a sheet for planarly diffusing the urine permeated through a partial region of the topsheet 20. Thanks to this sheet, the absorption body 40 can absorb the urine permeated through a partial region of the topsheet 20 in a wide region on the topsheet 20 side surface of the absorption body 40. The second sheet 50 is disposed across the front waist region 11, the crotch region 13 and the rear waist region 12.

For the second sheet 50, a nonwoven fabric having high liquid diffusibility, such as tissue, point bond nonwoven fabric and rayon-containing spun lace nonwoven fabric, is preferably used. In particular, the liquid diffusibility of the second sheet 50 is preferably higher than the liquid diffusibility of the topsheet 20. For example, in the case of using a spunbond nonwoven fabric for the topsheet 20, a tissue, a point bond nonwoven fabric, a spun lace nonwoven fabric (particularly, rayon-containing), which are higher in the liquid diffusibility than the spun bond nonwoven fabric, or a mixture thereof is preferably used for the second sheet 50.

The liquid diffusibility of the sheet can be evaluated, for example, by the Klemm water absorbency of the sheet measured in accordance with JIS P8141 "Paper and Paperboard—Water Absorbency Test Method—Klemm Method", since paper is a kind of nonwoven fabric. The Klemm water absorbency is a height to which water rises in 10 minutes due to a capillary phenomenon when the lower end of a specimen is vertically dipped in water, and a higher Klemm water absorbency of the sheet indicates higher diffusibility of the sheet. For example, the Klemm water absorbency of a tissue having a basis weight of 15 g/m$^2$ was 28 mm, the Klemm water absorbency of a spun lace nonwoven fabric (rayon-containing) having a basis weight of 38 g/m$^2$ was 118 mm, the Klemm water absorbency of a point bond nonwoven fabric having a basis weight of 23 g/m$^2$ was 36 mm, the Klemm water absorbency of an air-through nonwoven fabric having a basis weight of 25 g/m$^2$ was 3 mm, and the Klemm water absorbency of a spunbond nonwoven fabric having a basis weight of 20 g/m$^2$ was 2 mm. Accordingly, among these nonwoven fabrics, a spun lace nonwoven fabric (rayon-containing) having a highest Klemm water absorbency is most preferred as the sheet used for the second sheet 50, and a tissue and a point bond nonwoven fabric each having a high Klemm water absorbency are also preferred. However, an air-through nonwoven fabric and a spunbond nonwoven fabric each having a low Klemm water absorbency are not preferred as the sheet used for the second sheet 50. In general, the Klemm water absorbency is higher as the density of the nonwoven fabric is higher, and is more increased when the nonwoven fabric contains a water-absorbent fiber such as rayon.

The absorbent sheet 60 is a composite sheet where an absorbent polymer 61 is sandwiched between two liquid-pervious sheets 62 and 63. For example, a nonwoven fabric is used for the liquid-pervious sheets 62 and 63. Incidentally, the absorbent sheet may be produced by sandwiching an absorbent polymer by three or more liquid-pervious sheets. Also, the absorbent sheet may be produced by sandwiching an absorbent polymer by a folded liquid-pervious sheet. That is to say, the absorbent sheet is produced by sandwiching an absorbent polymer by at least one liquid-pervious sheet. The absorbent polymer is a polymer capable of absorbing water and is, for example, an absorbent macromolecular polymer having a three-dimensional network structure formed by appropriate crosslinking of water-soluble macromolecules. Such an absorbent macromolecular polymer absorbs several hundreds or thousands of times as much water as the volume before absorbing water but is substantially water-insoluble and does not release the once absorbed water even when some pressure is applied. Examples of the absorbent polymer include starch-based, acrylic acid-based or amino acid-based particulate or fibrous polymers. An absorbent polymer 61 is sandwiched by two liquid-pervious sheets 62 and 63 and then, these two liquid-pervious sheets 62 and 63 are joined, whereby the absorbent sheet 60 is produced. Accordingly, in order to prevent the absorbent polymer from spilling after sandwiching the absorbent polymer 61 between two liquid-pervious sheets 62 and 63, the particle diameter of the absorbent polymer is preferably large compared with the fiber interstices of the liquid-pervious sheets 62 and 63. For example, a spunbond nonwoven fabric, a point bond nonwoven fabric, an air-through nonwoven fabric or an SMS (spunbond-melt blown-spunbond) nonwoven fabric may be used for the liquid-pervious sheets 62 and 63. The liquid-pervious sheets 62 and 63 must have permeability to urine and therefore, they are preferably subjected to a hydrophilization treatment.

On the absorbent polymer 61-sandwiching surfaces of the liquid-pervious sheets 62 and 63, a plurality of longitudinally extending adhesive parts 82 and 83 aligned in the width direction are provided. Incidentally, the adhesive parts 82 and 83 may be provided on the absorbent polymer 61-sandwiching surface of one liquid-pervious sheet 62 and 63 out of the liquid-pervious sheets 62 and 63. The adhesive part 82 and 83 is formed, for example, by coating a hot-melt adhesive in a streak manner. Thanks to this adhesive, the absorbent polymer 61 is fixed to the liquid-pervious sheets 62 and 63. The coating method is not limited to the streaky coating method as long as it is a coating method capable of providing a region absent of the adhesive part, for example, intermittently disposing the adhesive part, since permeability of urine in the adhesive part 82 and 83 is poor. A non-contact coating method such as omega pattern coating may be also employed. The adhesive part 82 and 83 is intermittently provided in the later-described absorbent polymer-existing region 64, so that the absorbent polymer 61 can be prevented from being biased in the absorbent polymer-existing region 64. The adhesive part-to-adhesive part distance between adjacent adhesive parts of the adhesive parts 83 provided on the liquid-pervious sheet 63 on the second sheet 50 side is small compared with the adhesive part-to-adhesive part distance of the adhesive parts 82 provided on the liquid-pervious sheet 62 on the topsheet 20 side. Thanks to this configuration, the absorbent polymer 61 is evenly fixed to the liquid-pervious sheet 63 on the second sheet 50 side.

The absorbent sheet 60 is preferably disposed in at least a part of the rear waist region 12. Thanks to this configuration, when the wearer's urination orifice is contacted with the absorbent article 1, the urine excreted without permeating through the absorbent sheet 60 can be directly absorbed by the absorption body 40 (see FIG. 5), and when the wearer's urination orifice is not contacted with the absorbent article 1, the urine can be absorbed by the absorbent sheet 60 (see FIG. 6).

In the absorbent sheet 60, the absorbent polymer 61 is disposed in parts in a plurality of regions 64 (hereinafter, referred to as an "absorbent polymer-existing region"), and a region 65 having not disposed therein the absorbent polymer 61 (hereinafter, referred to as an "absorbent polymer-nonexisting region") is provided between respective absorbent polymer-existing regions 64. Thanks to this configuration, even when the absorbent polymer 61 in the absorbent polymer-existing region 64 fully swells by absorbing urine and cannot absorb urine any more, the urine passes through the absorbent polymer-nonexisting region 65 and is absorbed by the absorption body 40.

The widthwise central portion 610 in the absorbent polymer-existing region 64 is located on the rear side in a direction towards the edge of the rear waist region, compared with each of widthwise outward portions 620 relative to the widthwise central portion 610 in the absorbent polymer-existing region 64. Thanks to this configuration, when the wearer's urination orifice is contacted with the absorbent article 1, the excreted urine can be directly absorbed by the absorption body 40 without being absorbed by the absorbent polymer 61 in the absorbent polymer-existing region 64, and when the wearer's urination orifice is not contacted with the absorbent article 1, the urine can be absorbed by the absorbent polymer 61 in the absorbent polymer-existing region 64.

The planar shape of the absorbent polymer-existing region 64 is a nearly V-shape projecting in the direction from the front waist region 11 to the rear waist region 12 in the longitudinal direction of the absorbent article 1 and extending in the width direction of the absorbent article 1. That is, the planar shape of the absorbent polymer-existing region 64 is a nearly V-shape with the apex facing in the direction from the front waist region 11 to the rear waist region 12 in the longitudinal direction of the absorbent article 1. However, the absorbent polymer-existing region 64 most remote from the front waist region 11 has a shape formed by cutting out the widthwise center of the nearly V-shape to divide it into two regions. Since the nearly V-shape of the absorbent polymer-existing region 64 is a shape following the wearer's buttocks, the absorbent polymer-existing region 64 fits over the wearer's buttocks and a gap is scarcely produced between the wearer and the absorbent article 1. Incidentally, the shape of the absorbent polymer-existing region is not limited to the nearly V-shape as long as an absorbent polymer-nonexisting region is present. For example, the shape of the absorbent polymer-existing region may be a circular arc shape, a round shape, a rectangular shape or a triangular shape.

As described above, the absorbent sheet 60 is produced by sandwiching an absorbent polymer 61 by two liquid-pervious sheets 62 and 63 and then, joining these two liquid-pervious sheets 62 and 63. Accordingly, the region where the absorbent polymer 61 is sandwiched between two liquid-pervious sheets 62 and 63 is the absorbent polymer-existing region 64, and the region where two liquid-pervious sheets 62 and 63 are joined without sandwiching the absorbent polymer 61 between those two liquid-pervious sheets 62 and 63 is the absorbent polymer-nonexisting region 65. Joining of these two liquid-pervious sheets 62 and 63 requires strength high enough to withstand the expansion force due to swelling of the absorbent polymer 61. Otherwise, two liquid-pervious sheets 62 and 63 can become separated from each other due to swelling of the absorbent polymer 61 to produce a gap between the two liquid-pervious sheets 62 and 63 and allow intrusion of the absorbent polymer 61 into the gap, resulting in disappearance of the absorbent polymer-nonexisting region 65. For joining the liquid-pervious sheets 62 and 63 with strength as desired, a heat seal, a sonic seal, an adhesive or the like can be used.

In the case of joining the liquid-pervious sheets 62 and 63 with each other by a heat seal, when the linear pressure in the width direction of the heat seal is constant, uniform seal strength is achieved in whole. For this reason, the linear pressure in the width direction of the heat seal is preferably constant. For keeping a uniform linear pressure in the width direction of the heat seal, the total of the widthwise lengths of regions to be sealed must be made constant. For example, as described above, absorbent polymer-existing regions 64 are formed in a nearly V-shape or a nearly circular arc shape and aligned in the longitudinal direction, whereby the total of the widthwise lengths of the absorbent polymer-nonexisting regions 65 can be made substantially constant. In the case of joining the liquid-pervious sheets 62 and 63 with each other by using an adhesive, the adhesive is preferably of a type capable of exerting the strength even when wetted, because the liquid-pervious sheets 62 and 63 are in a wet state when the absorbent polymer 61 is swelled.

The absorbent polymer 61 swells once absorbing urine and therefore, in the absorbent polymer-existing region 64, the absorbent polymer 61 preferably reserves, between two liquid-pervious sheets 62 and 63, a volume large enough to enable fully swelling of the absorbent polymer 61. If the absorbent polymer 61 is densely packed too much between two liquid-pervious sheets 62 and 63, the absorbent polymer 61 cannot be completely swelled and in turn, the absorption ability of the absorbent polymer 61 may not be sufficiently utilized.

When the number of absorbent polymer-existing regions 64 in the absorbent sheet 60 is increased, the area of the absorbent polymer-nonexisting region 65 is increased, but the total amount by volume of the absorbent polymer 61 in the absorbent sheet 60 decreases and therefore, the amount of urine that can be absorbed by the absorbent sheet 60 becomes small. On the other hand, when the number of absorbent polymer-existing regions 64 in the absorbent sheet 60 is decreased, the total amount by volume of the absorbent polymer 61 in the absorbent sheet 60 is increased and the amount of urine that can be absorbed by the absorbent sheet 60 becomes large, but the area of the absorbent polymer-nonexisting region 65 decreases and it may not occur that after the absorbent polymer is swelled, urine permeates through the absorbent sheet 60 and is absorbed by the absorption body 40. Accordingly, the number of absorbent polymer-existing regions 64 need to be selected by considering the balance between the amount of urine that can be absorbed by the absorbent sheet 60 and the permeability to urine of the absorbent sheet 60 after the absorbent polymer 61 is swelled and by further considering the volume of the absorbent polymer 61 after swelling, which is dependent on the kind and charge amount of the polymer. For example, in the case of an absorbent sheet with a size of 180 mm×130 mm, 2 g of an absorbent polymer capable of absorbing 60 g of a normal saline solution per 1 g is disposed in parts in 5 absorbent polymer-existing regions, whereby an absorbent sheet well-balanced between the urine absorbability and permeability to urine after swelling of the absorbent polymer can be obtained. The percentage of the area of the absorbent polymer-existing regions 64 to the area of the absorbent sheet 60 preferably is 40 to 80%. When the percentage of the area of the absorbent polymer-existing regions 64 to the area of the absorbent sheet 60 is less than 40%, the urine absorbed by the absorption body 40 may wet the wearer's buttocks. When the percentage of the area of the absorbent polymer-existing regions 64 to the area of the absorbent sheet 60 is more than 80%, after the absorbent polymer is swelled, urine may not permeate through the absorbent sheet 60 and may not be absorbed by the absorption body 40.

The leak-preventive cuffs 70 prevent the excreted urine from leaking outside at a widthwise positions of the absorbent article 1. In both widthwise side parts of the absorbent article 1, a longitudinally extending leak-preventive cuff 70 is disposed. A hydrophobic nonwoven fabric such as SMS nonwoven fabric is used for the leak-preventive cuffs 70. A leak-preventive material such as waterproof film may be also used in place of SMS nonwoven fabric. The leak-preventive cuffs 70 are joined with the topsheet 20 or the backsheet 30 in the widthwise side parts of the absorbent article 1 by, for example, using an adhesive and have base end parts 74 and free end parts 75. The base end parts 74 are joined with the widthwise side parts of the absorbent article 1 and can be fixed using a heat seal in place of an adhesive. The base end part 74 may be also located at the side edges or backsheet surface of the absorbent article 1. The free end parts 75 are located on the widthwise inner sides of the absorbent article 1 relative to the base end parts 74. An elastic body 72 capable of extending in the longitudinal direction and fixed in an extended state is provided in the vicinity of the free end part 75 of each of the leak-preventive cuffs 70. Also, the regions 73 on the longitudinal end sides of the leak-preventive cuffs 70 are joined with the topsheet 20 by, for example, using an adhesive. When the elastic bodies 72 develops their contractive force, the free end parts 75 of the leak-preventive cuffs 70 excluding the regions 73 on the lengthwise end sides of the leak-preventive cuffs 70 rise from the topsheet 20 and prevent excreted urine from leaking at a widthwise position of the absorbent article 1. The leak-preventive cuffs 70 need not be disposed over the entire length of the absorbent article 1 and may be sufficient if they are disposed at least across crotch region 13 to the rear waist region 12.

As shown in FIG. 1, in the state of the elastic bodies 72 being not contracted, that is, in the state of the leak-preventive cuffs 70 being extended, each widthwise edge part 66 of the absorbent sheet 60 is located on the widthwise outer side relative to each free end parts 75 of the leak-preventive cuffs 70. When the absorbent article 1 is worn by a wearer, the leak-prevent cuffs 70 fall on the topsheet 20 and the widthwise outer sides of both edge parts 66 in the width direction of the absorbent sheet 60 are covered with the leak-preventive cuffs 70. Thanks to the presence of the leak-preventive cuffs 70 with low liquid permeability, even when urine seeps from the absorption body 40, the urine can be prevented from contacting with the skin. In the regions where the absorbent sheet 60 and the leak-preventive cuffs 70 are overlapped, even when urine seeps from the absorbent sheet 60, the leak-preventive cuffs 70 can be prevented from contacting with the skin. Particularly, in the region 73 on the longitudinal end sides of the leak-preventive cuffs 70, the leak-preventive cuffs 70 are adhered to the topsheet 20 or the backsheet 30 by using an adhesive and therefore, can be fixed so that both edge parts 66 of the absorbent sheet 60 can unfailingly overlap with the leak-preventive cuffs 70. This configuration also increases the effect of not allowing urine seeping from the absorption body 40 due to the body pressure imposed on the later-described absorbent sheet 60 to reach the wearer's skin and the effect of absorbing urine diffused by running down the wearer's skin.

Absorption of the excreted urine by the absorption article 1 in one embodiment of the present invention is described below by referring to the drawings.

Figure 5:
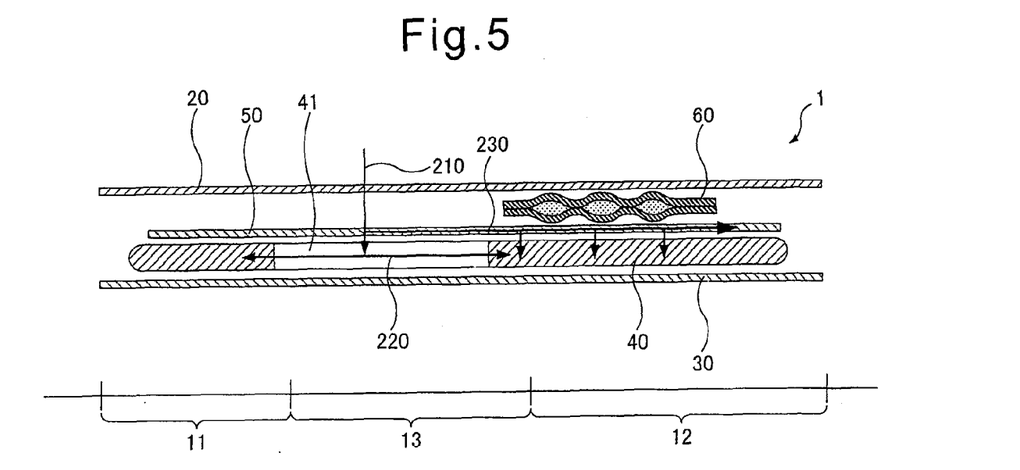
FIG. 5 is a view for explaining absorption of the excreted urine with the absorbent article according to one embodiment of the present invention when the wearer's urination orifice is contacted with the absorbent article.

In the case where the wearer's urination orifice is contacted with the absorbent article 1, as shown in FIG. 5, the excreted urine passes (arrow 210) through the topsheet 20 and the second sheet 50 from the urination region and reaches the absorption body 40. The urine reached the absorption body 40 is absorbed from the second sheet 50 side surface of the absorption body 40. Some urine reached (arrow 210) the penetration part 41 of the absorption body 40 is absorbed (arrow 220) from the side wall of the penetration part 41, and some urine reached the compressed groove 42 of the absorption body 40 is absorbed from the side wall of the compressed groove 42. By providing the penetration part 41 and/or the compressed groove 42 in the absorption body 40, the excreted urine is allowed to readily move in the longitudinal direction and therefore, diffusion of the excreted urine to the absorption body 40 is accelerated. Also, a part of the excreted urine diffuses (arrow 230) in the second sheet 50 after passing through the topsheet 20 and is absorbed by the absorption body 40. By allowing the excreted urine to diffuse in the second sheet 50, the excreted urine widely spreads on the second sheet 50 side surface of the absorption body 40. In turn, the area of the absorption body 40 surface for absorbing the excreted urine is increased and therefore, diffusion of the excreted urine to the absorption body 40 is accelerated.

The second sheet 50 is disposed on the side opposite the wearer side of the absorbent sheet 60 and this makes it difficult for the urine diffused in the second sheet 50 to reach the wearer's skin side due to the absorbent sheet 60. Because, when the wearer lies on his (her) back and a body pressure is imposed on the rear waist region 12 of the absorbent article 1 from the wearer's buttocks, the urine absorbed in the absorption body 40 seeps but the seeped urine hardly reaches the wearer's skin side due to the absorbent sheet 60. On the other hand, in the region of the crotch region 13, where the absorbent sheet 60 is not disposed, and the front waist region 11, a pressure is less likely to be imposed on the absorbent article 1 and it is lessened that the urine diffused in the second sheet 50 reaches the wearer's skin or the urine absorbed by the absorption body 40 seeps from the absorption body 40. In turn, the skin near the wearer's buttocks is kept dry and comfortable even after the urine is excreted, and the wearer's skin can be protected against irritation due to the excreted urine.

Figure 6:
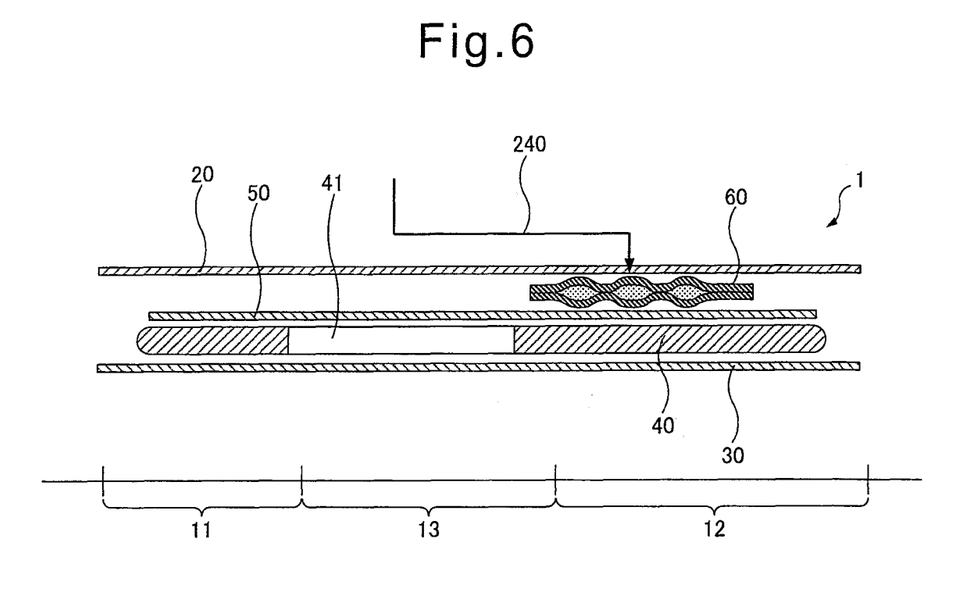
FIG. 6 is a view for explaining absorption of the excreted urine with the absorbent article according to one embodiment of the present invention when the wearer's urination orifice is not contacted with the absorbent article.

In the case where the wearer's urination orifice is not contacted with the absorbent article 1, for example, when the wearer lies on his(her) back, as shown in FIG. 6, the excreted urine runs down the wearer's skin to reach (arrow 240) the topsheet 20 in the buttock region. The urine reached the topsheet 20 is absorbed by the absorbent sheet 60. Also, as described above, the absorbent polymer has a property of not releasing the once absorbed water even upon application of some pressure and therefore, even when the wearer lies on his(her) back and a body pressure is imposed on the rear waist region 12 of the absorbent article 1 from the wearer's buttocks, the urine absorbed by the absorbent sheet 60 is less likely to seep from the absorbent sheet 60 due to the body pressure. In turn, the wearer's skin is kept dry and comfortable even after the urine is excreted, and the wearer's skin can be protected against irritation from the excreted urine. Particularly, in the case where the wearer is a wearer continuously put in a state of the wearer's urination orifice being not contacted with the absorbent article 1, for example, when the wearer is in a bedridden state, the absorbent article 1 is suitable, because the urine is excreted in a state of the wearer's urination orifice being not contacted with the absorbent article 1 or a body pressure is always imposed on the rear waist region 12 of the absorbent article 1 from the wearer's buttocks.

In the case where the urine excreted when the wearer's urination orifice is contacted with the absorbent article 1 is absorbed by the absorption body 40, it can be confirmed by a return amount test and a surface residual water test that the urine is less likely to seep from the absorption body 40 and reach the wearer's skin. Also, in the case where the urine excreted when the wearer's urination orifice is not contacted with the absorbent article 1 is absorbed by the absorption body 40, it can be confirmed by a return amount test that the urine is less likely to seep from the absorption body 40 and reach the wearer's skin. Details of the test method for the return amount test and surface residual water test are described in Examples later.

Due to the constitution of the absorbent article 1, in the case where artificial urine is dropped in the urination region and the artificial urine is absorbed by the absorption body 40, when the return amount of the artificial urine in the buttock region not more than 200 times less than than the return amount of the artificial urine in the urination region. The former is more preferably not more than 300 times less than, still more preferably not more than 600 times less, than the latter. Therefore, the urine excreted when the wearer's urination orifice is contacted with the absorbent article 1 is less likely to seep from the absorption body 40 after being absorbed by the absorption body 40 and reach the wearer's skin. That is, due to the constitution of the absorbent article 1, the return of urine in the buttock region is reduced even after urine is excreted, and the wearer's skin is kept dry and comfortable. In particular, when 400 ml of artificial urine is dropped in the urination region and the artificial urine is absorbed by the absorption body 40, the return amount of the artificial urine in the buttock region is 0.3 g or less.

Due to the constitution of the absorbent article 1, the return amount of the artificial urine in the buttock region at the time of dropping artificial urine in the buttock region and allowing the artificial urine to be absorbed by the absorption body 40 can take a value of 0.7 or less, 0.6 or less, or 0.5 or less, or 0.4 or less of the return amount of the artificial urine in the urination region at the time of dropping artificial urine in the urination region and allowing the artificial urine to be absorbed by the absorption body 40. Therefore, after the urine excreted when the wearer's urination orifice is not contacted with the absorption body 1 is absorbed by the absorption body 40, the urine is less likely to seep from the absorption body 40 and reach the wearer's skin. That is, due to the constitution of the absorbent article 1, the wearer's skin is kept dry and comfortable even after the urine is excreted.

Due to the constitution of the absorbent article 1, in the case of dropping artificial urine in the urination region and allowing the artificial urine to be absorbed by the absorption body 40, the surface residual water quantity in the buttock region can take a value of 0.8 or less, 0.7 or less, or 0.5 or less of the surface residual water quantity in the urination region. Therefore, after the urine excreted when the wearer's urination orifice is contacted with the absorbent article 1 is absorbed by the absorption body 40, the urine is less likely to seep from the absorption body 40 and reach the wearer's skin. That is, due to the constitution of the absorbent article 1, the wearer's skin is kept dry and comfortable even after the urine is excreted. In particular, due to the constitution of the absorbent article 1, when 400 ml of artificial urine is dropped in the urination region and the urine is absorbed by the absorption body 40, the water percentage on the topsheet surface in the buttock region can be about 50 mass % or less, about 40 mass % or less, or about 30 mass % or less.

The present invention is not limited to the urine-absorbing pad. The present invention may be, for example, an absorbent article such as disposable diaper, toilet training pant and incontinence brief.

It is also possible to combine the embodiment with one modification example or a plurality of modification examples. Modification examples may be also combined with each other in any combination.

The descriptions in the foregoing pages are only one example, and the invention is not limited to the above-described embodiments by any means.

EXAMPLES

The present invention is described in greater detail below by referring to Examples. However, the present invention is not limited to the following Examples.

Example 1

Return Amount Test

Using the following samples and test method, it was confirmed that when the wearer's urination orifice is contacted with the absorbent article and when the wearer's urination orifice is not contacted with the absorbent article, the excreted urine is not allowed to seep from the absorbent article and wet the wearer's buttocks (rewet).

Sample

A return amount test was performed using absorbent articles having the following constituent elements.

Topsheet: A hydrophilic spunbond nonwoven fabric having a basis weight of 20 $g/m^2$.

Absorbent sheet: A sheet obtained by sandwiching 2 g of an absorbent polymer between hydrophilic air-through nonwoven fabrics each having a basis weight of 25 $g/m^2$ and joining the nonwoven fabrics together.

Second sheet: A tissue having a basis weight of 15 $g/m^2$.

(1) In Case of Absorption Body Having a Water Retention Amount of 660 g

Absorption body: A stack obtained by stacking an upper-layer absorption body composed of a pulp having a basis weight of 278 $g/m^2$ and an absorbent polymer having a basis weight of 107 $g/m^2$ on a lower-layer absorption body composed of a pulp having a basis weight of 214 $g/m^2$ and an absorbent polymer having a basis weight of 80 $g/m^2$.

A size of the topsheet: 600 mm×180 mm.
A size of the absorbent sheet: 180 mm×130 mm.
A size of second sheet: 550 mm×160 mm.

(2) In Case of Absorption Body Having a Water Retention Amount of 450 g

Absorption body: A stack obtained by stacking an upper-layer absorption body composed of a pulp having a basis weight of 220 $g/m^2$ and an absorbent polymer having a basis weight of 82 $g/m^2$ on a lower-layer absorption body composed of a pulp having a basis weight of 180 $g/m^2$ and an absorbent polymer having a basis weight of 33 $g/m^2$.

A size of the topsheet: 550 mm×180 mm.
A size of the absorbent sheet: 180 mm×130 mm.
A size of second sheet: 500 mm×160 mm.

Test Method (1) A cylinder (diameter: 60 mm, weight: 550 g) is placed on the artificial urine dropping position of the absorbent article, and 80 ml of artificial urine is dropped by a burette at a rate of 150 ml/15 sec from 10 mm above the absorbent article substantially in the center part of the cylinder. This operation is performed 5 times every 5 minutes. Accordingly, 400 ml of artificial urine is dropped. The artificial urine is an aqueous solution prepared by dissolving 200 g of urea, 80 g of sodium chloride, 80 g of magnesium sulfate, 8 g of calcium chloride and about 1 g of a dye: Blue No. 1, in 10 liters of ion-exchanged water. Here, 400 ml is generally the amount of urine when the elderly urinates 3 to 4 times.

(2) At 5 minutes after charging 400 ml of artificial urine, a filter paper of 70 g (100 mm×100 mm) is placed on the measurement position, a weight of 3.5 kg with the bottom surface having a size of 100 mm×100 mm is placed thereon, and the artificial urine seeping from the absorbent article is absorbed by the filter paper.

(3) After leaving it to stand for 3 minutes, the weight of the filter paper is measured. The value obtained by subtracting the weight of filter paper before absorbing the artificial urine from the weight of the filtration paper having absorbed therein the artificial urine is the return amount. In the samples used here, absorption bodies having a water retention amount of 450 g and 660 g are used, and the amount of artificial urine is set to 400 ml, but in the case where the water retention amount is small due to low basis weight of the pulp or absorbent polymer of the absorption body or small size of the absorption body, the measurement can be performed by adjusting the amount of artificial urine in the range of 50 to 90 mass % of water retention amount of an absorption body.

The test was carried out at a temperature of 20° C. and a relative humidity of 60%. The filter paper is a qualitative filter paper for mid-grade filtration, manufactured by Advantec Toyo Kaisha, Ltd, the grade of which is No. 2. The No. 2 grade filter paper corresponds to a type-II filter paper defined in JIS P 3801.

Dropping Position

Figure 7A:
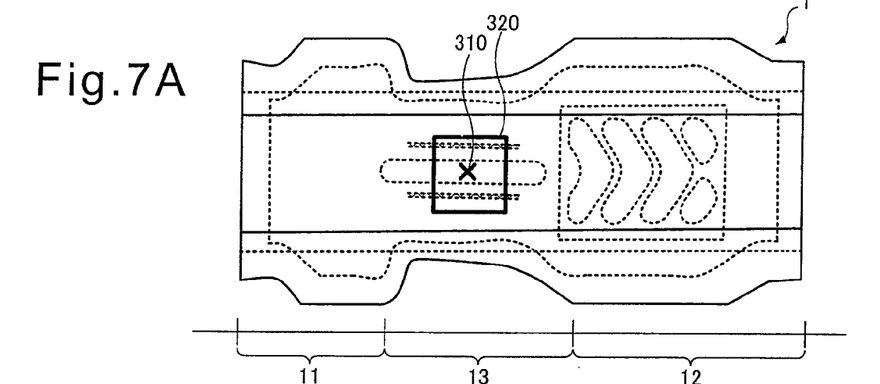
FIG. 7A is a view for explaining the dropping position and the measurement position.
Figure 7B:
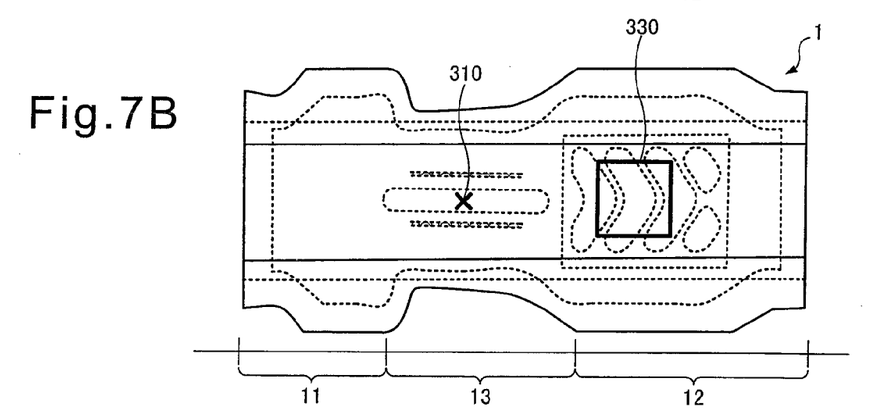
FIG. 7B is a view for explaining the dropping position and the measurement position.
Figure 7C:
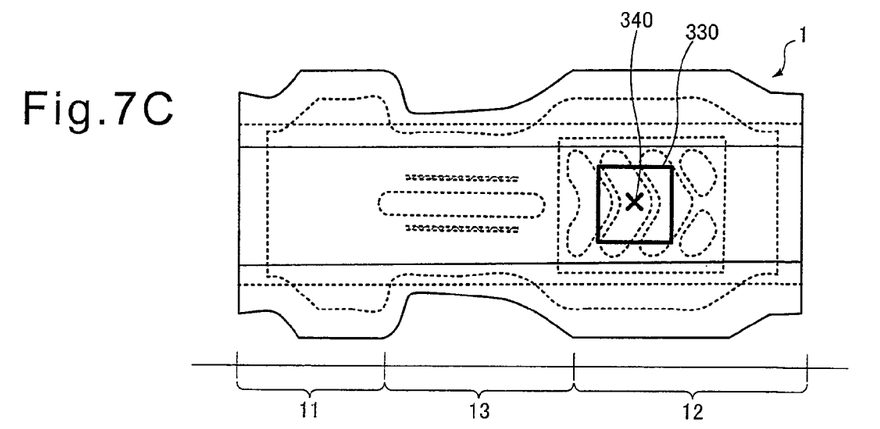
FIG. 7C is a view for explaining the dropping position and the measurement position.

As shown in FIGS. 7A-7C, the artificial urine was dropped to a position 310 in the urination region, for example, a position longitudinally away from the front waist region 11 side end of the absorbent article 1 by a distance of 39% of the longitudinal length of the absorbent article 1 and at the widthwise center of the absorbent article 1, and to a position 340 in the buttock region, for example, a position longitudinally away from the front waist region 11 side end of the absorbent article 1 by a distance of 60% of the longitudinal length of the absorbent article 1 and at the widthwise center of the absorbent 1. Incidentally, as long as the position to which the artificial urine is dropped lies within the urination region, the position is not limited to the position 310 and the position longitudinally away from the front waist region 11 side end of the absorbent article 1 by a distance of 39% of the longitudinal length of the absorbent article 1 and at the widthwise center of the absorbent article 1. Also, as long as the position to which the artificial urine is dropped lies within the buttock region, the position is not limited to the position 340 and the position longitudinally away from the front waist region 11 side end of the absorbent article 1 by a distance of 60% of the longitudinal length of the absorbent article 1 and at the widthwise center of the absorbent article 1.

Measurement Position

As shown in FIGS. 7A-7C, the predetermined regions 320 and 330 centering around the dropping positions 310 and 340, respectively, were taken as the measurement position. Incidentally, the measurement position is not limited to the region 320 as long as it is in the urination region, and also, the measurement position is not limited to the region 330 as long as it is in the buttock region.

Results

The results are shown in Table 1.

TABLE 1

Return Amount of Absorbent Article

| | In Case of Absorption Body Having Water Retention Amount of 660 g | | | In Case of Absorption Body Having Water Retention Amount of 450 g | | |
|---|---|---|---|---|---|---|
| | Dropping position | | | | | |
| | urination region | urination region | buttock region | urination region | urination region | buttock region |
| | Measurement position | | | | | |
| | urination region | buttock region | buttock region | urination region | buttock region | buttock region |
| Example 1 | 57.0 | 0.1 | 19.2 | 69.3 | 0.2 | 35.5 |
| Example 2 | 60.1 | 0.2 | 29.1 | 63.4 | 0.2 | 39.5 |
| Example 3 | 61.5 | 0.1 | 19.2 | 75.8 | 0.1 | 34.1 |
| Example 4 | 58.8 | 0.3 | 20.1 | 73.1 | 0.3 | 33.0 |
| Example 5 | 67.3 | 0.1 | 19.4 | 78.4 | 0.2 | 37.4 |
| Average value | 60.9 | 0.1 | 21.4 | 72.0 | 0.2 | 35.9 |

(1) In Case of Absorption Body Having a Water Retention Amount of 660 g (i) In the case where both the dropping position and the measurement position were in the urination region (see, FIG. 7A), the average value of the return amount was 60.9 g.

(ii) In the case where the dropping position was in the urination region and the measurement position was in the buttock region (see, FIG. 7B), the average value of the return amount was 0.1 g.

(ii) In the case where both the dropping position and the measurement position were in the buttock region (see, FIG. 7C), the average value of the return amount was 21.4 g.

Accordingly, when artificial urine was dropped in the urination region and the artificial urine was absorbed by the absorption body, the average value of the artificial urine return amount in the buttock region was 609 times less than the average value of the artificial urine return amount in the urination region, and the maximum value of the artificial urine return amount in the buttock region was 195 times less than the minimum value of the artificial urine return amount in the urination region. Also, when artificial urine was dropped in the buttock region and the artificial urine was absorbed by the absorption body, the average value of the artificial urine return amount in the buttock region was 0.35 (2.85 times less than) of the average value of the artificial urine return amount in the urination region in case of dropping artificial urine in the urination region and allowing the artificial urine to be absorbed by the absorption body, and the maximum value of the artificial urine return amount in the buttock region was 0.50 (2.01 times less than) of the minimum value of the artificial urine return amount in the urination region in case of dropping artificial urine in the urination region and allowing the artificial urine to be absorbed by the absorption body.

(2) In Case of Absorption Body Having a Water Retention Amount of 450 g (i) In the case where the dropping position was in the urination region and the measurement position was in the urination region (see, FIG. 7A), the average value of the return amount was 72.0 g.

(ii) In the case where the dropping position was in the urination region and the measurement position was in the buttock region (see, FIG. 7B), the average value of the return amount was 0.2 g.

(ii) In the case where both the dropping position was in the buttock region and the measurement position was in the buttock region (see, FIG. 7C), the average value of the return amount was 35.9 g.

Accordingly, when artificial urine was dropped in the urination region and the artificial urine was absorbed by the absorption body, the average value of the artificial urine return amount in the buttock region was 360 times less than the average value of the artificial urine return amount in the urination region, and the maximum value of the artificial urine return amount in the buttock region was 218 times less than the minimum value of the artificial urine return amount in the urination region. Also, when artificial urine was dropped in the buttock region and the artificial urine was absorbed by the absorption body, the average value of the artificial urine return amount in the buttock region was 0.50 (2.01 times less than) of the average value of the artificial urine return amount in the urination region in case of dropping artificial urine in the urination region and allowing the artificial urine to be absorbed by the absorption body, and the maximum value of the artificial urine return amount in the buttock region was 0.62 (1.61 times less than) of the minimum value of the artificial urine return amount in the urination region in case of dropping artificial urine in the urination region and allowing the artificial urine to be absorbed by the absorption body.

Example 2

Surface Residual Water Test

Using the following samples and test method, it was confirmed that when the wearer's urination orifice is contacted with the absorbent article in a state approximated to the worn state, the excreted urine is not allowed to seep from the absorbent article and wet the wearer's buttocks.

Test Method

Figure 8:
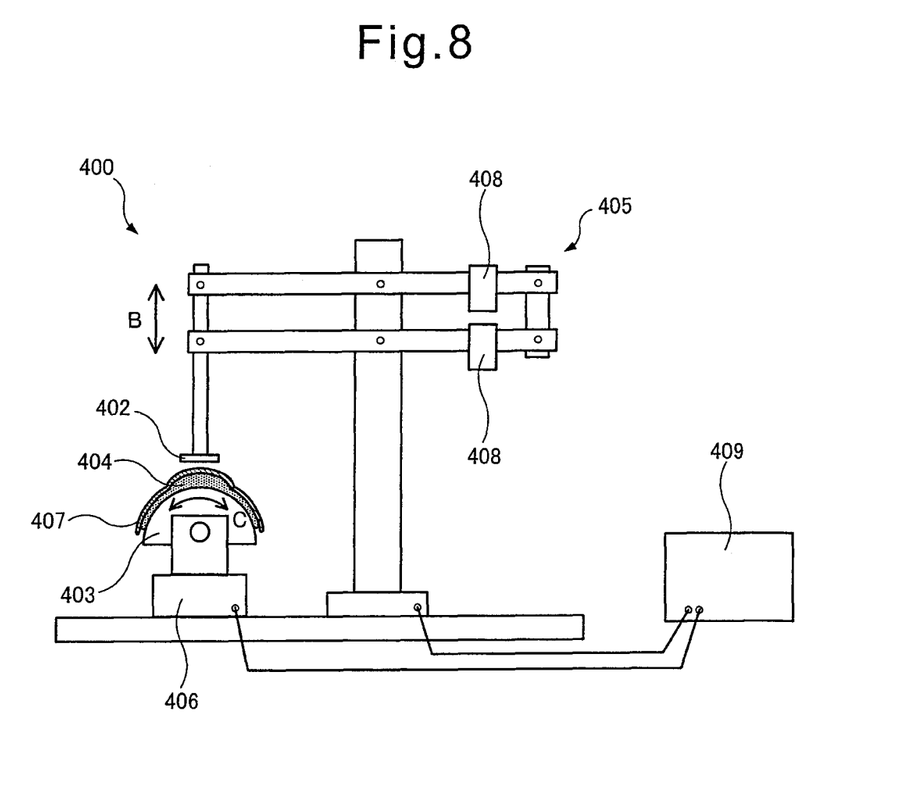
FIG. 8 is a view showing a state quantity distribution measurement apparatus for measuring the surface residual water of the absorbent article.

The method for measuring the surface residual water by a state quantity distribution measurement apparatus is described by referring to FIG. 8. FIG. 8 is a view showing a state quantity distribution measurement apparatus 400 for measuring the surface residual water of the absorbent article. The water quantity distribution measurement apparatus 400 comprises a sensor 402 for measuring the status quantity of the sample, a sample stand 403 for placing thereon a measurement sample composed of the absorbent article, which is a sample stand having a convex surface on which the sample is placed, a support mechanism 405 for supporting the sensor such that the contact pressure of the sensor with the sample is kept substantially constant, a transfer mechanism 406 for transferring at least one member of the sensor and the sample such that the sensor is transferred relative to the sample, and a measurement mechanism 409 for measuring the status quantity of the sample at a plurality of positions by the sensor while transferring the sensor relative to the sample by controlling the transfer mechanism, and thereby determining the status quantity of the sample.

The sensor 402 is a capacitance-type moisture sensor. The sample stand 403 has a true half-cylinder shape formed by cutting a true cylinder along a plane passing through the central axis line. Furthermore, the support mechanism 405 is a balance capable of adjusting the load applied to the sample 4 by the position of a weight 408 and can apply a constant load in the vertical direction denoted by B in FIG. 8 (hereinafter, sometimes referred to as "the direction B").

The transfer mechanism 406 can rotate the sample stand 403 along the direction C around the central axis line of the true cylinder and at the same time, can cause the sample stand 403 to move back and forth in parallel with the central axis line of the true cylinder, that is, in the front-back direction in FIG. 8. The transfer mechanism 406 rotates the sample stand 403 in the direction C and furthermore, causes the sample stand 403 to move back and force in the front-back direction, whereby the status quantity distribution of the sample can be evaluated.

To the measurement mechanism 409, the sensor 402 is connected through the support mechanism 405, and the transfer mechanism 406 is connected directly. The sample 404 is set on the sample stand 403, and an insulating film 407 is disposed between the sensor 402 and the sample 404 and covers the sample 404.

The procedure of measuring the surface residual water percentage of the sample 404 is as follows. First, a status quantity distribution measurement apparatus 400 shown in FIG. 8 is prepared. Next, a sample 404 is placed on the convex surface of the sample stand 403, an insulating film 407 is placed on the sample 404, and a sensor 402 is placed above the sample 404 with the intervention of the insulating film 407. Subsequently, the measurement mechanism 409 is operated to control the transfer mechanism 406 so as to rotate the sample stand 403 in the direction C around the central axis line of the true cylinder of the sample stand 403 and at the same time, transfer the sample stand 403 in the front-to-back direction. Along with this, the water percentage of the sample 404 is measured at a plurality of positions by the sensor 402 and by combining the values obtained, the water percentage distribution of the sample 404 is determined.

A measurement example of the status quantity distribution measurement apparatus described above is illustrated below. Incidentally, the voltage (V) quantified by the sensor 402 is converted into the water percentage according to the indices shown below.

Silcot (trademark) (produced by Unicharm Corporation) was impregnated with a given amount of water to produce standard samples of indices 1 to 6 having different water percentages. Each standard sample was left standing at 20° C. for one day in a tightly closed state.

A water quantity measurement apparatus shown in FIG. 8 was prepared, and each of the standard samples of indices 1 to 6 was placed on the sample stand of the water quantity measurement apparatus and measured for the water percentage.

The results are shown in Table 2 below.

TABLE 2

Relationship Between Water Percentage and Voltage

| | Index | | | | | | |
|---|---|---|---|---|---|---|---|
| | 1 | 2 | 3 | 4 | 5 | 6 | 7 |
| Water percentage (mass %) | 8.23 | 33.6 | 52.6 | 66.5 | 73.5 | 79.7 | 83.1 |
| Voltage (V) | 0.18 | 0.65 | 1.70 | 1.87 | 2.21 | 2.44 | 2.72 |

Based on the data above, a calibration curve from an origin was prepared by a least-squares method, as a result, a relational expression of y=32.7x was obtained between the water percentage y and the voltage x.

Sample

A surface residual water test was performed using an absorbent article having the same constituent elements as those of the sample in case of an absorption body having a water retention amount of 660 g, used in the return amount test.

Test Method (1) The absorbent article is curved in U-shape at an angle of R=110° to bulge toward the lower side by arranging the skin-non-contact side of the crotch region of the absorbent article to face downward. The measurement is performed by curving the absorbent article in U-shape so as to measure the absorbent article in a state approximated to the actually worn state, and this is a state capable of, despite urine dropping in the urination region, producing urine that is absorbed after flowing in the direction toward the rear waist region on the absorbent article surface.

(2) 80 ml of the above-described artificial urine is dropped by a burette at a rate of 150 ml/15 sec. This operation is performed 5 times every 5 minutes. Accordingly, 400 ml of artificial urine is dropped.

(3) At 5 minutes after charging 400 ml of artificial urine, in a state of the absorbent article being spread flat, a weight of 2,100 g (60 mm×100 mm, 35 g/cm$^2$) is placed thereon to apply pressure for 30 seconds.

(4) After removing the weight, the water percentage at the measurement position is measured using the status quantity distribution measurement apparatus.

Dropping Position

As shown in FIGS. 7A-7C, the artificial urine was dropped to a position 310 in the urination region, for example, a position longitudinally away from the front waist region 11 side end of the absorbent article 1 by a distance of 39% of the longitudinal length of the absorbent article 1, and to a position 340 in the buttock region, for example, a position longitudinally away from the front waist region 11 side end of the absorbent article 1 by a distance of 60% of the longitudinal length of the absorbent article 1. The position 310 to which the artificial urine was dropped is a position simulating the urination region, and the position 340 to which the artificial urine was dropped is a position simulating the buttock region.

Measurement Position

Similarly to the return amount test above, the predetermined regions 320 and 330 shown in FIGS. 7A-7C centering around the dropping positions 310 and 340, respectively, were taken as the measurement position.

While sliding the sample stand 403 in steps of 55 mm, 15 points in the region were measured and the average value of the measurement results at 15 points was taken as the water percentage on the topsheet surface.

The results are shown in Table 3.

TABLE 3

Water Percentage of Absorbent Article

| Dropping position | urination region | urination region |
|---|---|---|
| Measurement position | urination region | buttock region |
| Water percentage (mass %) | 62.1 | 49.7 |
| Voltage (V) | 1.90 | 1.52 |

(i) In the case where the dropping position was in the urination region and the measurement position was in the urination region (see, FIG. 7A), the water percentage was 62.1 mass %.

(ii) In the case where the dropping position was in the urination region and the measurement position was in the buttock region (see, FIG. 7B), the water percentage was 49.7 mass %.

Accordingly, when artificial urine was dropped in the urination region and the artificial urine was absorbed by the absorption body, the water percentage in the buttock region was 0.8 (1.25 times less than) of the water percentage in the urination region.

Example 3

Horny Layer Water Quantity Test

The results in the return amount test and surface residual water test above reveal the followings.

(i) Even when the wearer's body pressure is imposed to urge the urine absorbed in the absorbent article region covering the wearer's buttocks to return to the wearer's skin, the absorbent polymer of the absorbent sheet absorbs the urine and can reduce the return amount.

(ii) The water on the topsheet on the rear waist side where an absorbent sheet is disposed is absorbed by the absorbent sheet and is reduced.

(iii) Even when the excreted urine runs down the wearer's skin and is diffused on the absorbent sheet, the urine is absorbed by the absorbent sheet.

In order to confirm whether or not the absorbent article in one embodiment of the present invention having these effects can significantly reduce the water quantity of the wearer's horny layer in practice, a horny layer water quantity test was performed.

Sample

A horny layer water quantity test in case of an absorption body having a water retention amount of 450 g was performed using an absorbent article having the same constituent elements as those of the sample used in the return amount test.

Test Method

The above-described absorbent article was used by 40 females for 4 weeks, and 4 weeks after the start of use, the water quantity of the wearer's horny layer was evaluated. Also, for comparison, a conventional absorbent article (produced by Unicharm Corporation, "Lifree Zai Anshin Nyoutori Pad") was used by 40 females for 4 weeks, and 4 weeks after the start of use, the water quantity of the wearer's horny layer was evaluated. The horny layer water quantity was relatively evaluated by measuring the skin impedance by means of an impedance meter, skikon-200 (manufactured by IBS). The measurement was performed on the coccyx and sacrum portions in the wearer's buttocks part and on the wearer's back.

Results

The average value of the horny layer water quantity in the coccyx portion when using the absorbent article in one embodiment of the present invention was 141 μS, the average value of the horny layer water quantity in the sacrum portion was 119 μS, and, the average value of the horny layer water quantity in the back was 26 μS. On the other hand, the average value of the horny layer water quantity in the coccyx portion when using the conventional absorbent article was 212 μS, the average value of the horny layer water quantity in the sacrum portion was 234 μS, and the average value of the horny layer water quantity in the back was 33 μS. These results reveal that by wearing the absorbent article in one embodiment of the present invention, the horny layer water quantity can be reduced and the excessively moist condition of the buttocks can be improved. Also, the horny layer water quantity in the buttocks part in case of not wearing the absorbent article is generally from 80 to 100 μS, and this reveals that by wearing the absorbent article in one embodiment of the present invention, even when the absorbent article is worn, each water quantity in the wearer's buttocks part can be maintained at almost the same horny layer water quantity as the horny layer water quantity in the buttocks part in case of not wearing an absorbent article.

In general, if the horny layer water quantity of the buttocks skin is too large, the moist condition may prune the cutaneous surface and the skin may be inflamed, for example, by miscellaneous bacteria, digestive enzymes in feces, or physical irritation due to friction•compression. However, by using the absorbent article in one embodiment of the present invention, the buttocks skin can be prevented from being put into a state with an excessively large horny layer water quantity and the skin can be kept from being inflamed, for example, by miscellaneous bacteria, digestive enzymes in feces, or physical irritation due to friction compression.

DESCRIPTION OF NUMERICAL REFERENCES

1 Absorbent article
20 Topsheet
30 Backsheet
40 Absorption body
41 Penetration part
42 Compressed groove
50 Second sheet
60 Absorbent sheet
61 Absorbent polymer
62, 63 Liquid-pervious sheet
64 Absorbent polymer-existing region
65 Absorbent polymer-nonexisting region
66 Edge part
70 Leak-preventive cuff
71 Edge part
72 Elastic body
400 Status quantity distribution measurement apparatus
402 Sensor
403 Sample stage
405 Support mechanism
406 Transfer mechanism
409 Measurement mechanism

The invention claimed is:
1. An absorbent article consisting of a front waist region, a rear waist region and a crotch region located between these regions in a longitudinal direction from a front side to a rear side, comprising:
 a liquid-pervious topsheet,
 a backsheet,
 an absorption body intervening between said topsheet and said backsheet, and
 an absorbent sheet between said topsheet and said absorption body, comprising at least one liquid-pervious sheet having sandwiched thereby an absorbent polymer, wherein:
  said topsheet, said backsheet and said absorption body are disposed across said front waist region, said crotch region and said rear waist region,
  said absorbent sheet is disposed in at least a part of said rear waist region,
  the absorbent article has a urination region that is a region having not disposed therein said absorbent sheet and covering the wearer's urination orifice, and a buttock region that is a region having disposed therein said absorbent sheet and covering the wearer's buttocks,
  when an artificial urine is dropped and absorbed in said urination region, the return amount of said artificial urine in said buttock region takes a value of not more than 200 times less than the return amount of said artificial urine in said urination region,
  said artificial urine comprises 200 g of urea, 80 g of sodium chloride, 80 g of magnesium sulfate, 8 g of calcium chloride and about 1 g of a dye per 10 liters of ion-exchanged water,
  the return amount of said artificial urine in said buttock region when said artificial urine is dropped and absorbed in said buttock region takes a value of 0.7 or less of the return amount of said artificial urine in said urination region when said artificial urine is dropped and absorbed in said urination region,
  said absorption body has a penetration part which penetrates therethrough in a thickness direction at a widthwise central position and which extends longitudinally across the crotch region up to or into the front waist region.

2. The absorbent article as claimed in claim 1, wherein said at least one liquid-pervious sheet is a folded liquid-pervious sheet or two liquid-pervious sheets.

3. The absorbent article as claimed in claim 2, wherein when 400 ml of said artificial urine is dropped and absorbed in said urination region, the return amount of said artificial urine in said buttock region is 0.3 g or less.

4. The absorbent article as claimed in claim 3, wherein:
 the absorbent article further comprises a second sheet between said absorbent sheet and said absorption body,
 said second sheet is disposed across said front waist region, said crotch region and said rear waist region, and
 said second sheet is higher in the liquid diffusibility than said topsheet.

5. The absorbent article as claimed in claim 2, wherein:
 the absorbent article further comprises a second sheet between said absorbent sheet and said absorption body,
 said second sheet is disposed across said front waist region, said crotch region and said rear waist region, and
 said second sheet is higher in the liquid diffusibility than said topsheet.

6. The absorbent article as claimed in claim 2, wherein said absorbent sheet has an absorbent polymer-existing region in which said absorbent polymer is sandwiched by said at least one liquid-pervious sheet and an absorbent polymer-nonexisting region in which said absorbent polymer is not sandwiched by said at least one liquid-pervious sheet.

7. The absorbent article as claimed in claim 1, wherein when 400 ml of said artificial urine is dropped and absorbed in said urination region, the return amount of said artificial urine in said buttock region is 0.3 g or less.

8. The absorbent article as claimed in claim 7, wherein:
 the absorbent article further comprises a second sheet between said absorbent sheet and said absorption body,
 said second sheet is disposed across said front waist region, said crotch region and said rear waist region, and
 said second sheet is higher in the liquid diffusibility than said topsheet.

9. The absorbent article as claimed in claim 1, wherein:
 the absorbent article further comprises a second sheet between said absorbent sheet and said absorption body,
 said second sheet is disposed across said front waist region, said crotch region and said rear waist region, and
 said second sheet is higher in the liquid diffusibility than said topsheet.

10. The absorbent article as claimed in claim 1, wherein said absorbent sheet has an absorbent polymer-existing region in which said absorbent polymer is sandwiched by said at least one liquid-pervious sheet and an absorbent polymer-nonexisting region in which said absorbent polymer is not sandwiched by said at least one liquid-pervious sheet.

11. The absorbent article as claimed in claim 10, wherein the planar shape of said absorbent polymer-existing region is a nearly V-shape with an apex facing in the direction from said front waist region to said rear waist region in the longitudinal direction of said absorbent article.

12. The absorbent article as claimed in claim 1, wherein:
the percentage of the area of the absorbent polymer-existing regions to the area of the absorbent sheet is 40 to 80%.

13. An absorbent article consisting of a front waist region, a rear waist region and a crotch region located between these regions in a longitudinal direction from a front side to a rear side, comprising:
a liquid-pervious topsheet,
a backsheet,
an absorption body intervening between said topsheet and said backsheet, and
an absorbent sheet between said topsheet and said absorption body, comprising said at least one liquid-pervious sheet having sandwiched thereby an absorbent polymer is present between said topsheet and said absorption body,
wherein:
said absorbent sheet is disposed in at least a part of said rear waist,
the absorbent article has a urination region that is a region having not disposed therein said absorbent sheet and covering the wearer's urination orifice, and a buttock region that is a region having disposed therein said absorbent sheet and covering the wearer's buttocks,
when an artificial urine is dropped and absorbed from said urination region, the surface residual water quantity in said buttock region takes a value of 0.8 or less of the surface residual water quantity in said urination region,
said artificial urine comprises 200 g of urea, 80 g of sodium chloride, 80 g of magnesium sulfate, 8 g of calcium chloride and about 1 g of a dye per 10 liters of ion-exchanged water,
said absorption body has a penetration part which penetrates therethrouqh in a thickness direction at a widthwise central position and which extends longitudinally across the crotch region up to or into the front waist region.

14. The absorbent article as claimed in claim 13, wherein said at least one liquid-pervious sheet is a folded liquid-pervious sheet or two liquid-pervious sheets.

15. The absorbent article as claimed in claim 14, wherein 400 ml of said artificial urine is dropped and absorbed from said urination region, the surface water percentage in said buttock region is 50 mass% or less.

16. The absorbent article as claimed in claim 15, wherein:
the absorbent article further comprises a second sheet between said absorbent sheet and said absorption body,
said second sheet is disposed across said front waist region, said crotch region and said rear waist region, and
said second sheet is higher in the liquid diffusibility than said topsheet.

17. The absorbent article as claimed in claim 14, wherein:
the absorbent article further comprises a second sheet between said absorbent sheet and said absorption body,
said second sheet is disposed across said front waist region, said crotch region and said rear waist region, and
said second sheet is higher in the liquid diffusibility than said topsheet.

18. The absorbent article as claimed in claim 13, wherein 400 ml of said artificial urine is dropped and absorbed from said urination region, the surface water percentage in said buttock region is 50 mass% or less.

19. The absorbent article as claimed in claim 18, wherein:
the absorbent article further comprises a second sheet between said absorbent sheet and said absorption body,
said second sheet is disposed across said front waist region, said crotch region and said rear waist region, and
said second sheet is higher in the liquid diffusibility than said topsheet.

20. The absorbent article as claimed in claim 13, wherein:
the absorbent article further comprises a second sheet between said absorbent sheet and said absorption body,
said second sheet is disposed across said front waist region, said crotch region and said rear waist region, and
said second sheet is higher in the liquid diffusibility than said topsheet.

* * * * *